(12) United States Patent
Minamoto et al.

(10) Patent No.: US 8,685,713 B2
(45) Date of Patent: Apr. 1, 2014

(54) BLOOD TESTING BOTTOMED TUBE, STOPPER FOR BLOOD TESTING BOTTOMED TUBE AND BLOOD TESTING CONTAINER

(75) Inventors: Masaaki Minamoto, Shunan (JP); Hironobu Isogawa, Shunan (JP)

(73) Assignee: Sekisui Chemical Co., Ltd., Osaka (JP)

( * ) Notice: Subject to any disclaimer, the term of this patent is extended or adjusted under 35 U.S.C. 154(b) by 140 days.

(21) Appl. No.: 12/168,767

(22) Filed: Jul. 7, 2008

(65) Prior Publication Data

US 2008/0274540 A1 Nov. 6, 2008

Related U.S. Application Data

(63) Continuation of application No. 10/507,740, filed as application No. PCT/JP03/06722 on May 29, 2003, now Pat. No. 7,595,028.

(30) Foreign Application Priority Data

May 29, 2002 (JP) ................................. 2002-155856

(51) Int. Cl.
  *C12M 1/34* (2006.01)
  *C12M 3/00* (2006.01)
(52) U.S. Cl.
  USPC ...................................................... 435/287.9
(58) Field of Classification Search
  USPC .................. 600/573; 422/102, 61, 99, 44–48; 435/4, 287.9; 436/174, 176, 63, 66; 604/4.01–6.16
  See application file for complete search history.

(56) References Cited

U.S. PATENT DOCUMENTS

| | | | |
|---|---|---|---|
| 2,677,700 A | 5/1954 | Lundsted et al. | |
| 3,769,152 A | 10/1973 | Samuelson et al. | |
| 4,153,739 A | 5/1979 | Kessler | |
| 4,373,009 A | 2/1983 | Winn | |
| 4,465,480 A | 8/1984 | Tanaka et al. | |
| 4,605,917 A | 8/1986 | Ide et al. | |
| 4,731,242 A | 3/1988 | Palinczar | |
| 4,770,779 A * | 9/1988 | Ichikawa et al. | 210/516 |
| 4,852,584 A | 8/1989 | Selby | |

(Continued)

FOREIGN PATENT DOCUMENTS

DE  19630879  2/1998
EP  1199104  4/2002

(Continued)

OTHER PUBLICATIONS

Supplementary European Search Report dated Feb. 1, 2011 issued in counterpart Application No. EP03730685.

(Continued)

*Primary Examiner* — Brian Szmal
*Assistant Examiner* — Huong Q. Nguyen
(74) *Attorney, Agent, or Firm* — Novak Druce Connolly Bove + Quigg LLP

(57) ABSTRACT

The present invention relates to a blood testing bottomed tube, which comprises a tubular member having an open one end and closed another end, and a coating layer formed on at least a part to be contacted with blood on said tubular member, said coating layer being made of a polyoxyalkylene alkyl ether or a polyoxyalkylene glycol ether, the present invention also relates to a stopper for a blood testing bottom tube and a blood testing container.

3 Claims, 1 Drawing Sheet

(56) References Cited

U.S. PATENT DOCUMENTS

| | | |
|---|---|---|
| 4,856,533 A | 8/1989 | Anraku et al. |
| 4,948,525 A | 8/1990 | Sasaki et al. |
| 4,985,026 A | 1/1991 | Kasai et al. |
| 5,306,270 A | 4/1994 | Mccartney et al. |
| 5,344,611 A | 9/1994 | Vogler et al. |
| 5,352,583 A | 10/1994 | Sakata et al. |
| 5,509,899 A | 4/1996 | Fan et al. |
| 5,510,237 A | 4/1996 | Isogawa et al. |
| 5,533,518 A | 7/1996 | Vogler |
| 5,554,315 A | 9/1996 | Tonomura et al. |
| 5,650,234 A | 7/1997 | Dolence et al. |
| 5,683,771 A | 11/1997 | Tropsha |
| 5,962,620 A | 10/1999 | Reich et al. |
| 5,981,293 A | 11/1999 | Charlton |
| 6,050,956 A | 4/2000 | Ikegami et al. |
| 6,077,235 A | 6/2000 | Serpentino et al. |
| 6,155,991 A | 12/2000 | Beat et al. |
| 6,290,655 B1 | 9/2001 | Serpentino et al. |
| 6,300,135 B1 | 10/2001 | Isogawa et al. |
| 6,395,227 B1 | 5/2002 | Kiser et al. |
| 6,447,835 B1 | 9/2002 | Wang et al. |
| 6,506,340 B1 * | 1/2003 | Tsai et al. ................. 422/45 |
| 6,534,016 B1 | 3/2003 | Cohen et al. |
| 6,673,852 B1 | 1/2004 | Suda et al. |
| 6,793,885 B1 | 9/2004 | Yokoi et al. |
| 6,903,243 B1 | 6/2005 | Burton |
| 7,015,262 B2 | 3/2006 | Leong |
| 2001/0006700 A1 | 7/2001 | Nazarova et al. |
| 2003/0105199 A1 * | 6/2003 | Furukawa et al. ............ 524/386 |
| 2005/0106071 A1 | 5/2005 | Minamoto et al. |
| 2006/0177564 A1 | 8/2006 | Diaz et al. |

FOREIGN PATENT DOCUMENTS

| | | |
|---|---|---|
| JP | 58-105063 A | 6/1983 |
| JP | 58105063 | 6/1983 |
| JP | 58-195151 A | 11/1983 |
| JP | 58195151 | 11/1983 |
| JP | 61-128944 A | 6/1986 |
| JP | 61128944 | 6/1986 |
| JP | H5073174 B | 3/1993 |
| JP | Hei 10-248828 | 9/1998 |
| WO | WO-0071181 | 11/2000 |

OTHER PUBLICATIONS

Office Action issued in related European Application No. 03730685.9 on Jul. 19, 2011.

* cited by examiner

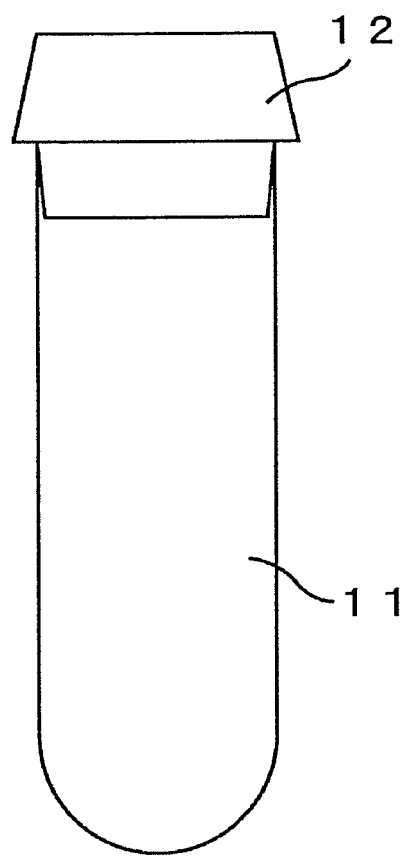

BLOOD TESTING BOTTOMED TUBE, STOPPER FOR BLOOD TESTING BOTTOMED TUBE AND BLOOD TESTING CONTAINER

This is a continuation of application Ser. No. 10/507,740 filed Sep. 15, 2004, which is a 371 of PCT/JP03/06722, filed May 29, 2003, claiming priority of Japanese Patent Application No. 2002-155856 filed May 29, 2002, the entire disclosures of these prior applications being considered part of the disclosure of this continuation application and are incorporated herein by reference.

TECHNICAL FIELD

The present invention relates to a blood testing bottomed tube causing no adhesion of blood clot and the like in a blood test and exerting no influence on the tested value, a stopper for a blood testing bottomed tube capable of easily plugging a blood testing bottomed tube, causing no adhesion of blood clot and the like in a blood test, exerting no influence on the tested value, and also causing no stickiness and label-peeling of a blood testing bottomed tube, and a blood testing container comprising the blood testing bottomed tube and the stopper for a blood testing bottomed tube.

BACKGROUND ART

Recently, with progress of test technologies, blood tests such as a serum biochemistry test, serum immunology test, blood cell test and the like are widely spread, contributing significantly to prevention of diseases and early diagnosis. As blood collecting tubes and preservation containers for blood used in blood tests, specimen containers in tests, and the like, there are often used blood testing containers comprising a blood testing bottomed tube in the form of bottomed tube having open one end and closed another end, and a stopper for a blood testing bottomed tube sealing the opening of the blood testing bottomed tube.

Conventionally, as the blood testing bottomed tube, those made of glass, or plastics such as polyethylene terephthalate, polystyrene, polymethyl methacrylate, polyethylene are often used, and blood testing bottomed tubes made of plastics sometimes exert a significant influence on the test value of a blood test by adhesion of blood clot and blood cells on the inner wall surface in a blood test. Particularly, when blood clot and blood cells adhered cannot be peeled even by centrifugal separation, hemolysis arises, blood blot and blood cells remaining in a blood testing bottomed tube peel before a test and mix into serum and plasma for test, resultantly, a correct test cannot be conducted, in some cases.

Then, in a blood testing bottomed tube intending extraction of serum and plasma, for the purpose of cleanly peeling adhered blood by centrifugal separation, a coating agent is usually applied on the wall surface of a blood testing bottomed tube.

As such coating agents used in a blood testing bottomed tube, there are generally used hydrophobic silicone oils such as polydimethylsiloxane and the like, and hydrophilic modified silicone oils.

However, when a hydrophobic silicone oil is used, there is a problem that blood clot and fibrin easily adhere to a blood testing bottomed tube, or the foam in blood is not de-foamed for a long period of time, by this, a significant influence is exerted on the results of a blood test. A hydrophilic modified silicone oil is eluted in blood or causes a mutual action with blood, and depending on test items, the test results are influenced in some cases, becoming problematic.

Further, also on the stopper for a blood testing bottomed tube for sealing the opening of a blood testing bottomed tube, a coating agent is usually applied in the same manner as for a blood testing bottomed tube. This is applied for the purpose of performing a role as a lubricant in plugging a blood testing bottomed tube with a stopper, in addition to cleanly peeling blood adhered to a stopper by centrifugal separation.

As such a coating agent on a stopper, hydrophobic silicone oils such as polydimethylsiloxane and the like are used. Japanese Kokoku Publication Hei-5-73174 discloses a polyoxyalkylene modified silicone oil as a coating agent for a stopper, and such a hydrophilizated modified silicone oils is also used.

However, there is a problem with the hydrophobic silicone oil that a significant influence is exerted on the result of a blood test by a tendency of adhesion of blood clot and fibrin to a stopper easily and by a fact that foam in blood is not de-foamed for a long period of time. The hydrophilic modified silicone oil has a problem that it is eluted in blood and causes a mutual action with blood, resultantly, depending on test items, an influence is exerted on the test result, in some cases. Further, these silicone oils have a problem that in production, in packing and transportation, and in use, by contact of a blood testing bottomed tube with a stopper, the silicone on the stopper moves to the blood testing bottomed tube, resultantly, the blood testing bottomed tube becomes sticky, and it becomes difficult to paste labels on the blood testing bottomed tube.

SUMMARY OF THE INVENTION

In view of above-mentioned problems, the object of the present invention is to provide a blood testing bottomed tube which causes no adhesion of blood clot and the like and no foam in blood in a blood test, and even in the case of generation of foam in blood, de-foams this quickly, and does not exert an influence on the test value, a stopper for a blood testing bottomed tube which can plug a blood testing bottomed tube, causes no adhesion of blood clot and the like and no foam in blood in a blood test, and even in the case of generation of foam in blood, de-foams this quickly, and does not exert an influence on the test value, further, does not cause label peeling and stickiness on a blood testing bottomed tube, and a blood testing container comprising the above-mentioned blood testing bottomed tube and the above-mentioned stopper for a blood testing bottomed tube.

The first aspect of the present invention is a blood testing bottomed tube, which comprises a tubular member having an open one end and closed another end, and a coating layer formed on at least a part to be contacted with blood on said tubular member, said coating layer being made of a polyoxyalkylene glycol and/or a polyoxyalkylene glycol derivative.

It is preferable that the polyoxyalkylene glycol derivative is a polyoxyalkylene alkyl ether having a viscosity at 25° C. of 30 to 50000 mPs and/or a polyoxyalkylene glycol ether having a viscosity at 25° C. of 30 to 50000 mPs, and it is preferable that the polyoxyalkylene glycol derivative is polyoxypropylene butyl ether and/or polyoxypropylene glyceryl ether.

The second aspect of the present invention is a blood testing bottomed tube, which comprises a tubular member having an open one end and closed another end, and a coating layer formed on at least a part to be contacted with blood on said tubular member, said coating layer being made of at least one compound selected from the group consisting of polypropylene glycol, polyethylene glycol and polyoxyethylene-polyoxypropylene condensates.

The third aspect of the present invention is a stopper for a blood testing bottomed tube, which comprises a member in the form of plug, and a coating layer made of a polyoxyalkylene glycol and/or a polyoxyalkylene glycol derivative formed on the surface of said member in the form of plug.

It is preferable that the polyoxyalkylene glycol derivative is a polyoxyalkylene alkyl ether having a viscosity at 25° C. of 30 to 50000 mPs and/or a polyoxyalkylene glycol ether having a viscosity at 25° C. of 30 to 50000 mPs, it is preferable that the polyoxyalkylene glycol derivative is polyoxypropylene butyl ether and/or polyoxypropylene glyceryl ether.

The fourth aspect of the present invention is a stopper for a blood testing bottomed tube, which comprises a member in the form of plug, and a coating layer made of at least one compound selected from the group consisting of polypropylene glycol, polyethylene glycol and polyoxyethylene-polyoxypropylene condensates, formed on the surface of said member in the form of plug.

It is preferable that the member in the form of plug is made of rubber or thermoplastic elastomer, and it is preferable that the rubber is butyl rubber, chlorinated butyl rubber or brominated butyl rubber.

A blood testing container, which comprises the blood testing bottomed tube according to the first aspect of the present invention and the stopper for a blood testing bottomed tube according to the third aspect of the present invention is also one of the present invention.

A blood testing container, which comprises the blood testing bottomed tube according to the first aspect of the present invention and the stopper for a blood testing bottomed tube according to the fourth aspect of the present invention is also one of the present invention.

A blood testing container, which comprises the blood testing bottomed tube according to the second aspect of the present invention and the stopper for a blood testing bottomed tube according to the third aspect of the present invention is also one of the present invention.

A blood testing container, which comprises the blood testing bottomed tube according to the second aspect of the present invention and the stopper for a blood testing bottomed tube according to the fourth aspect of the present invention is also one of the present invention.

BRIEF DESCRIPTION OF THE DRAWING(S)

FIG. 1 is a schematic view showing a vacuum blood collecting tube manufactured in an example.

DETAILED DISCLOSURE OF THE INVENTION

The present invention will be illustrated in detail below.

The blood testing bottomed tube of the present invention, comprises a tubular member having an open one end and closed another end, and a coating layer formed on at least parts to be contacted with blood on the above-mentioned tubular member.

The above-mentioned tubular member is not particularly restricted providing it is in the form of tube having an open one end and closed another end and capable of being used as a blood testing bottomed tube, and for example, there are mentioned those formed continuously of the same material, those obtained by clogging one end of tubes having open both ends with a stopper and the like, and other members. Above all, those formed continuously of the same material are preferable since they show general purpose, excellent in handling, and give excellent productivity. It is preferable that a stopper used for those obtained by clogging one end of tubes having open both ends with a stopper and the like is the stopper for a blood testing bottomed tube of the present invention described later.

The material of the above-mentioned tubular member or the material of a tube when the above-mentioned tubular member is one obtained by clogging one end of a tube having open both ends with a stopper and the like is not particularly restricted, and examples thereof include polyolefin resins such as polyethylene, polypropylene and the like; polystyrene resins; saturated polyester resins such as polyethylene terephthalate (PET), polyethylene naphthalate (PEN) and the like; thermoplastic resins such as polymethyl methacrylate resins, polyacrylonitrile resins and the like; thermosetting resins such as unsaturated polyester-based resins, epoxy-based resins, epoxy-acrylate resins and the like; modified natural resins such as cellulose acetate, cellulose propionate, ethylcellulose, ethylchitin and the like, in addition to glass. Above all, saturated polyester resins such as PET, PEN and the like are preferable due to an excellent gas barrier property and an excellent molding property. These may be used alone or in combination of two or more.

The above-mentioned coating layer has a role of enabling removal of blood adhere on a blood testing bottomed tube easily by an operation such as centrifugal separation and the like.

The above-mentioned coating layer is made, in the case of the blood testing bottomed tube according to the first aspect of the present invention, of a polyoxyalkylene glycol and/or a polyoxyalkylene glycol derivative, and in the case of the blood testing bottomed tube according to the second aspect of the present invention, of at least one compound selected from the group consisting of polypropylene glycol, polyethylene glycol and polyoxyethylene-polyoxypropylene condensates.

By using that made of such compounds as the above-mentioned coating layer, the above-mentioned role of the coating layer is satisfied, and simultaneously, deficiencies such as an influence on a blood test, a fact that foam in blood is not de-foamed for a long period of time, and the like, which are problems of a conventional blood testing bottomed tubes can be settled.

In the blood testing bottomed tube according to the first aspect of the present invention, the above-mentioned polyoxyalkylene glycol is a polymer of an alkylene oxide. The above-mentioned polymer may be a random copolymer or block copolymer.

The above-mentioned alkylene oxide is not particularly restricted, and for example, ethylene oxide, propylene oxide and the like are listed. Above all, suitable are polymers of propylene oxide, or polymers composed of ethylene oxide and propylene oxide, and for example, a polyoxyethylene-polyoxypropylene random copolymer and the like are mentioned.

The above-mentioned polyoxyalkylene glycol derivative is not particularly restricted, and for example, polyoxyalkylene alkyl ether, polyoxyalkylene glycol ether and the like are listed.

As the alkyl ether component of the above-mentioned polyoxyalkylene alkyl ether, for example, those obtained by etherifying monohydric alcohols such as butanol, propanol and the like are listed. As the above-mentioned polyoxyalkylene alkyl ether, for example, polyoxypropylene butyl ether of the following formula (1), polyoxyethylene polyoxypropylene butyl ether of the following formula (2), and the like are listed.

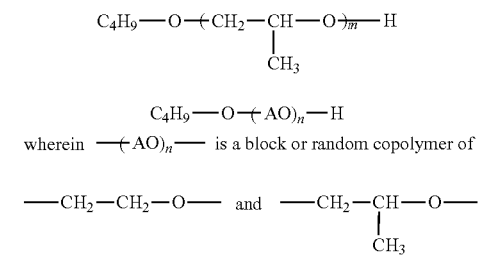

$$C_4H_9-O-(CH_2-CH(CH_3)-O)_m-H \quad (1)$$

$$C_4H_9-O-(AO)_n-H \quad (2)$$

wherein —(AO)$_n$— is a block or random copolymer of

—CH$_2$—CH$_2$—O— and —CH$_2$—CH(CH$_3$)—O—

In the formula (1) and formula (2), m and n represent an integer.

As the glycol ether component of the above-mentioned polyoxyalkylene glycol ether, for example, those obtained by etherifying ethylene glycol, propylene glycol and glycerin, and the like are listed. As the above-mentioned polyoxyalkylene glycol ether, for example, polyoxypropylene glyceryl ether of the following formula (3), polyoxyethylene polyoxypropylene glyceryl ether of the following formula (4), and the like are listed.

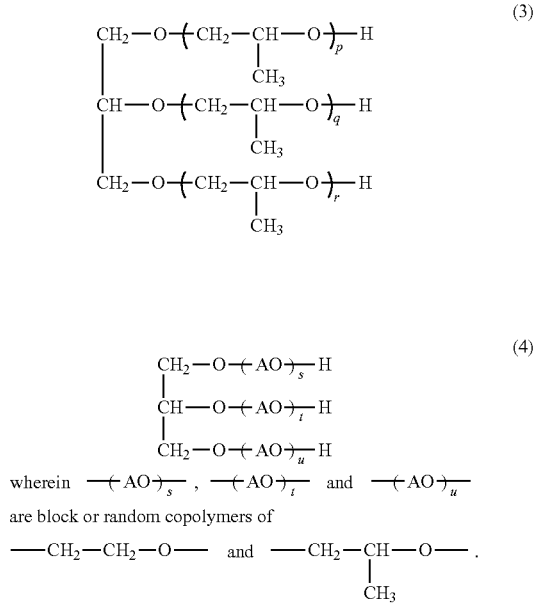

$$(3)$$

$$\begin{array}{l} CH_2-O-(CH_2-CH(CH_3)-O)_p-H \\ CH-O-(CH_2-CH(CH_3)-O)_q-H \\ CH_2-O-(CH_2-CH(CH_3)-O)_r-H \end{array}$$

$$(4)$$

$$\begin{array}{l} CH_2-O-(AO)_s-H \\ CH-O-(AO)_t-H \\ CH_2-O-(AO)_u-H \end{array}$$

wherein —(AO)$_s$—, —(AO)$_t$— and —(AO)$_u$— are block or random copolymers of

—CH$_2$—CH$_2$—O— and —CH$_2$—CH(CH$_3$)—O—.

In the formula (3) and formula (4), p, q, r, s, t and u represent an integer.

Above all, polyoxypropylene butyl ether and/or polyoxypropylene glyceryl ether is suitable. These may be used alone or in combination of two or more.

The viscosity of the above-mentioned polyoxyalkylene alkyl ether and/or polyoxyalkylene glycol ether is not particularly restricted, and the preferable lower limit is 30 mPs and the upper limit is 50000 mPs at 25° C. When it is less than 30 mPs, the stability and blood peeling property as a coating layer may become insufficient in some cases, and when it is more than 50000 mPs, lubricity in plugging with a stopper may be inferior in some cases. For example, polyoxypropylene butyl ether having a viscosity of about 40 to 1000 mPs, polyoxyethylene polyoxypropylene butyl ether having a viscosity of about 30 to 2000 mPs, polyoxypropylene glyceryl ether having a viscosity of about 200 to 700 mPs, and polyoxyethylene polyoxypropylene glyceryl ether having a viscosity of about 300 to 40000 mPs, are suitable.

In the blood testing bottomed tube according to the second aspect of the present invention, the preferable lower limit of the average molecular weight of the above-mentioned polypropylene glycol is 300, and the preferable upper limit thereof is 4000, and the more preferable lower limit thereof is 1500. The preferable lower limit of the average molecular weight of the above-mentioned polyethylene glycol is 400, and the preferable upper limit thereof is 6000.

As the above-mentioned polyoxyethylene-polyoxypropylene condensate, for example, a block copolymer obtained by adding ethylene oxide, for imparting hydrophilicity, to polypropylene glycol as a hydrophobic group, and the like are listed.

The above-mentioned polyoxyethylene-polyoxypropylene condensate preferably contains ethylene oxide in an amount of less than 70 wt %. When the content of ethylene oxide is 70 wt % or more, it becomes solid to make the coating layer fragile, in some cases. When it is less than 70 wt %, the coating layer is excellent in strength and stability. The preferable lower limit is 5 wt %, and the more preferably lower limit is 10 wt %.

The preferable lower limit of the average molecular weight of the above-mentioned polyoxyethylene-polyoxypropylene condensate is 1000, the upper limit thereof is 20000, and the more preferable upper limit thereof is 6000.

When a material easily soluble in water is used as the above-mentioned coating layer, there is a possibility that the material contained in the above-mentioned coating layer is eluted in blood, to exert an influence on the test value of a blood test, therefore, it is preferable to use materials hardly soluble or insoluble in water as the material of the above-mentioned coating layer. By this, it is hard to elute in blood, and application thereof to wider test region becomes possible.

On the other hand, when the above-mentioned coating layer is made of a material utterly insoluble in water, an action of de-foaming foamed blood is poor, and foam in blood is not settled for a long period of time in many cases. For example, it is also undesirable to use a cross-linking type material insoluble in blood. When foam in blood is problematic, it is effective to use a material hardly soluble but being slightly dissolved in blood to manifest a de-foaming action. For further enhancing balance of abilities, it is further effective to blend a hardly soluble material and an insoluble material.

The weight per unit area of the above-mentioned coating layer is not particularly restricted, and the preferable lower limit thereof is 0.1 μg per cm$^2$ of the surface area of a blood testing bottomed tube of the present invention, and the preferable upper limit thereof is 1000 μg. When it is less than 0.1 μg, the stability and blood peeling property as the coating layer may become insufficient in some cases, and when it is more than 1000 μg, there is a possibility of occurrence of problems such as too increase in the thickness of the coating layer, peeling of parts of the coating layer, and the like. It is more preferably from 1 to 100 μg.

The method for manufacturing a blood testing bottomed tube of the present invention is not particularly restricted, and there are mentioned, for example, methods in which a substance used as a raw material for the above-mentioned coating layer is dissolved or dispersed in a suitable medium to prepare coating liquid, this coating liquid is coated on the surface of a tubular member by applying this coating liquid on the surface of a tubular member, immersing a tubular member in the coating liquid, spraying the coating liquid on a tubular member, or adding a tubular member and the coating liquid in a rotary type stirring container and the like and mixing them, or by other means, then, the liquid is dried by room temperature drying, heat drying or vacuum drying and the like, and other methods. Further, a substance used as a raw material for the above-mentioned coating layer may be coated directly on the surface of a tubular member without using a medium.

In a blood testing bottomed tube of the present invention, as long as the above-mentioned coating layer is formed on at least parts to be contacted with blood on a tubular member, other formation parts are not particularly restricted, and the coating layer may be formed on the whole surface of a tubular member.

The medium for the above-mentioned coating liquid is not particularly restricted, and examples thereof include water, alcohols such as methanol, ethanol and the like, and toluene, xylene, ethylene glycol, propylene glycol and the like. It is preferable to select a medium in which raw material substances of the coating layer are uniformly dissolved or dispersed and which is excellent in wettability against a tubular member.

The concentration of the above-mentioned coating liquid is not particularly restricted, and the preferable low limit thereof is 0.01 wt %, and the upper limit thereof is 10 wt %.

When materials hardly soluble or insoluble in water are used as a substance to be used as a raw material for the above-mentioned coating layer, listed as the method for preparing a uniform coating liquid are, for example, a method for emulsification using an emulsifier, a method for dispersion utilizing forced stirring and ultrasonic wave in water, and the like, in addition to a method for using a medium capable of dissolving such materials.

The above-mentioned emulsifier is not particularly restricted, and there are mentioned as typical emulsifiers, for example, glycerin fatty acid ester, sucrose fatty acid ester, sorbitan fatty acid ester, propylene glycol fatty acid ester, lecithin, saponin, polyvinyl alcohol and the like.

As the above-mentioned emulsifier, it is preferable to select agents of which influence on the test value of a blood test is as low as possible so as not to limit the application range.

When a material having a polyoxyalkylene structure and having a cloud point such as polyoxyethylene is used, even if insoluble in water at room temperature, uniform dissolution in water can be attained by cooling to the cloud point or lower.

The blood testing bottomed tube of the present invention shows no adhesion of blood clot and the like and exerts no influence on the test value since the tube comprises a tubular member, and a coating layer made of a polyoxyalkylene glycol and/or a polyoxyalkylene glycol derivative formed on at least parts to be contacted with blood on the above-mentioned tubular member, or a coating layer made of at least one compound selected from the group consisting of polypropylene glycol, polyethylene glycol and polyoxyethylene-polyoxypropylene condensates. Also, there occurs no condition under which foam in blood is not de-foamed for a long period of time.

As the stopper used for sealing a blood testing bottomed tube of the present invention, suitable are those made of rubbers such as natural rubber, butyl rubber, chlorinated butyl rubber, brominated butyl rubber, silicone rubber and the like, and styrene-based, vinyl chloride-based, olefin-based, urethane-based, polyester-based and polyamide-based elastomers.

It is more preferable to use the stopper for a blood testing bottomed tube of the present invention described later.

When the blood testing bottomed tube is a blood collecting tube, the pressure in the blood testing bottomed tube can be reduced to give a vacuum blood collecting tube. Further, various chemicals are allowed to be accommodated in the above-mentioned blood testing bottomed tube depending on the object. The above-mentioned chemical is not particularly restricted, and for example, a coagulation accelerator for collecting serum, anticoagulant for preventing coagulation of blood, and the like are listed, and a serum separating agent, plasma separating agent and the like may also be accommodated.

The third aspect of the present invention is a stopper for a blood testing bottomed tube, comprising a member in the form of plug, and a coating layer made of a polyoxyalkylene glycol and/or a polyoxyalkylene glycol derivative formed on the surface of the above-mentioned member in the form of plug.

The fourth aspect of the present invention is a stopper for a blood testing bottomed tube, comprising a member in the form of plug, and a coating layer made of at least one compound selected from the group consisting of polypropylene glycol, polyethylene glycol and polyoxyethylene-polyoxypropylene condensates, formed on the surface of the above-mentioned member in the form of plug.

The stopper for a blood testing bottomed tube of the present invention comprises a member in the form of plug and a coating layer formed on the surface of the member in the form of plug.

The above-mentioned member in the form of plug is not particularly restricted, and for example, rubber, thermoplastic elastomers, and other plastics, and the like are listed.

The above-mentioned rubber is not particularly restricted, and for example, natural rubber, butyl rubber, chlorinated butyl rubber, brominated butyl rubber, silicone rubber and the like are listed. Above all, butyl rubber, chlorinated butyl rubber and brominated butyl rubber excellent in gas barrier property are suitable for applications requiring the gastightness of a vacuum blood collecting tube and the like.

As the above-mentioned thermoplastic elastomer, for example, styrene, vinyl chloride, olefin, urethane, polyester and polyamide elastomers are listed.

The above-mentioned coating layer acts as a lubricant in plugging a blood testing bottomed tube with a stopper, at the same time, plays a role of allowing blood adhered on a stopper to be removed easily.

The above-mentioned coating layer is made, in the case of the stopper for a blood testing bottomed tube according to the third aspect of the present invention, of a polyoxyalkylene glycol and/or a polyoxyalkylene glycol derivative, and in the case of the stopper for a blood testing bottomed tube according to the fourth aspect of the present invention, of at least one compound selected from the group consisting of polypropylene glycol, polyethylene glycol and polyoxyethylene-polyoxypropylene condensates.

By using that made of such compounds as the above-mentioned coating layer, the above-mentioned role of the coating layer is satisfied, and simultaneously, an influence on a blood test, generation of stickiness on a blood testing bottomed tube, and the like which are problems of conventional stoppers can be resolved.

In the stopper for a blood testing bottomed tube according to the third aspect of the present invention, the above-mentioned polyoxyalkylene glycol is a polymer of an alkylene oxide. The above-mentioned polymer may be a random copolymer or block copolymer.

The above-mentioned alkylene oxide is not particularly restricted, and for example, ethylene oxide, propylene oxide and the like are listed. Above all, suitable are polymers of propylene oxide, or copolymers of ethylene oxide and propylene oxide, and for example, a polyoxyethylene-polyoxypropylene random copolymer and the like are mentioned.

The above-mentioned polyoxyalkylene glycol derivative is not particularly restricted, and for example, polyoxyalkylene alkyl ether, polyoxyalkylene glycol ether and the like are listed.

As the alkyl ether component of the above-mentioned polyoxyalkylene alkyl ether, for example, those obtained by etherifying monohydric alcohols such as butanol, propanol and the like are listed. As the above-mentioned polyoxyalkylene alkyl ether, for example, polyoxypropylene butyl ether, polyoxyethylene polyoxypropylene butyl ether, and the like are listed.

As the glycol ether component of the above-mentioned polyoxyalkylene glycol ether, for example, those obtained by etherifying ethylene glycol, propylene glycol and glycerin, and the like are listed. As the above-mentioned polyoxyalkylene glycol ether, for example, polyoxypropylene glyceryl ether, polyoxyethylene polyoxypropylene glyceryl ether, and the like are listed.

Above all, polyoxypropylene butyl ether and/or polyoxypropylene glyceryl ether is suitable. These may be used alone or in combination of two or more.

The viscosity of the above-mentioned polyoxyalkylene alkyl ether and/or polyoxyalkylene glycol ether is not particularly restricted, and the preferable lower limit is 30 mPs and the upper limit is 50000 mPs at 25° C. When it is less than 30 mPs, the stability, lubricity and blood peeling property as a coating layer may become insufficient in some cases, and when it is more than 50000 mPs, lubricity may be inferior in some cases. For example, polyoxypropylene butyl ether having a viscosity of about 40 to 1000 mPs, polyoxyethylene polyoxypropylene butyl ether having a viscosity of about 30 to 2000 mPs, polyoxypropylene glyceryl ether having a viscosity of about 200 to 700 mPs, and polyoxyethylene polyoxypropylene glyceryl ether having a viscosity of about 300 to 40000 mPs, are suitable.

In the stopper for a blood testing bottomed tube according to the fourth aspect of the present invention, the preferable lower limit of the average molecular weight of the above-mentioned polypropylene glycol is 300, and the preferable upper limit thereof is 4000, and the more preferable lower limit thereof is 1500. The preferable lower limit of the average molecular weight of the above-mentioned polyethylene glycol is 400, and the preferable upper limit thereof is 6000.

As the above-mentioned polyoxyethylene-polyoxypropylene condensate, for example, a block copolymer obtained by adding ethylene oxide, for imparting hydrophilicity, to polypropylene glycol as a hydrophobic group, and the like are listed.

The above-mentioned polyoxyethylene-polyoxypropylene condensate preferably contains ethylene oxide in an amount of less than 70 wt %. When the content of ethylene oxide is 70 wt % or more, it becomes solid to make the coating layer fragile, in some cases. When it is less than 70 wt %, the coating layer is excellent in strength, stability, and lubricity in plugging a blood testing bottomed tube with a stopper. The preferable lower limit is 5 wt %, and the more preferably lower limit is 10 wt %.

The preferable lower limit of the average molecular weight of the above-mentioned polyoxyethylene-polyoxypropylene condensate is 1000, the upper limit thereof is 20000, and the more preferable upper limit thereof is 6000.

When a material easily soluble in water is used as the above-mentioned coating layer, there is a possibility that the material contained in the above-mentioned coating layer is eluted in blood, to exert an influence on the test value of a blood test, therefore, it is preferable to use materials hardly soluble or insoluble in water as the material of the above-mentioned coating layer. By this, it is hard to elute in blood, and application thereof to wider test region becomes possible.

On the other hand, when the above-mentioned coating layer is made of a material utterly insoluble in water, an action of de-foaming foamed blood is poor, and foam in blood is not settled for a long period of time in many cases. For example, a cross-linking type coating material not eluted utterly in blood is judged to be undesirable. When foam in blood is problematical, it is effective to use a material hardly soluble but being slightly dissolved in blood to manifest a de-foaming action. For further enhancing balance of abilities, it is further effective to blend a hardly soluble material and an insoluble material.

The weight per unit area of the above-mentioned coating layer is not particularly restricted, and the preferable lower limit thereof is 1 μg per $cm^2$ of the surface area of a blood testing bottomed tube of the present invention, and the preferable upper limit thereof is 1000 μg. When it is less than 1 μg, the stability and blood peeling property as the coating layer may become insufficient in some cases, and when it is more than 1000 μg, there is a possibility of occurrence of problems such as too increase in the thickness of the coating layer, peeling of parts of the coating layer, and the like. It is more preferably from 5 to 100 μg.

The method for manufacturing a stopper for a blood testing bottomed tube of the present invention is not particularly restricted, and there are mentioned, for example, methods in which a substance used as a raw material for the above-mentioned coating layer is dissolved or dispersed in a suitable medium to prepare coating liquid, this coating liquid is coated on the surface of a member in the form of plug by applying this coating liquid on the surface of a member in the form of plug, immersing a member in the form of plug in the coating liquid, spraying the coating liquid on a member in the form of plug, or adding a member in the form of plug and the coating liquid in a rotary type stirring container and the like and mixing them, or by other means, then, the liquid is dried by room temperature drying, heat drying or vacuum drying and the like, and other methods.

Further, a substance used as a raw material for the above-mentioned coating layer may be coated directly on the surface of a stopper without using a medium.

The medium for the above-mentioned coating liquid is not particularly restricted, and examples thereof include water, alcohols such as methanol, ethanol and the like, and toluene, xylene, ethylene glycol, propylene glycol and the like. It is preferable to select a medium in which raw material substances of the coating layer are uniformly dissolved or dispersed and which is excellent in wettability against a member in the form of plug.

The concentration of the above-mentioned coating liquid is not particularly restricted, and the preferable low limit thereof is 0.01 wt %, and the upper limit thereof is 10 wt %.

When materials hardly soluble or insoluble in water are used as a substance to be used as a raw material for the above-mentioned coating layer, listed as the method for preparing a uniform coating liquid are, for example, a method for emulsification using an emulsifier, a method for dispersion utilizing forced stirring and ultrasonic waver in water, and the like, in addition to a method for using a medium capable of dissolving such materials.

In the stopper for a blood testing bottomed tube of the present invention, it is preferable that the above-mentioned coating layer is provided on at least parts having a possibility of contact with blood accommodated in a blood testing bottomed tube, further, provided also on parts of a stopper to be contacted with the inner surface of a blood testing bottomed tube in plugging with the stopper. Further, the coating layer may also be formed on the whole surface of a stopper.

The above-mentioned emulsifier is not particularly restricted, and there are mentioned as typical emulsifiers, for example, glycerin fatty acid ester, sucrose fatty acid ester, sorbitan fatty acid ester, propylene glycol fatty acid ester, lecithin, saponin, polyvinyl alcohol and the like.

As the above-mentioned emulsifier, it is preferable to select agents of which influence on the test value of a blood test is as low as possible so as not to limit the application range.

When a material having a polyoxyalkylene structure and having a cloud point such as polyoxyethylene is used, even if insoluble in water at room temperature, uniform dissolution in water can be attained by cooling to the cloud point or lower.

The stopper for a blood testing bottomed tube of the present invention can plug a blood testing bottomed tube, causes no adhesion of blood clot and the like in a blood test, and causes no foaming in blood, and even if foam in blood occurs, de-foams this quickly, further, is not eluted into blood to exert an influence on the test value, since the body comprises a member in the form of plug, and a coating layer made of a polyoxyalkylene glycol and/or a polyoxyalkylene glycol derivative formed on the surface of the member in the form of plug, or a coating layer made of at least one compound selected from the group consisting of polypropylene glycol, polyethylene glycol and polyoxyethylene-polyoxypropylene condensates. Also, there occurs no condition under which it migrates onto a blood testing bottomed tube to cause stickiness on the blood testing bottomed tube or a difficulty of pasting labels on the blood testing bottomed tube.

It is suitable to use the stopper for a blood testing bottomed tube of the present invention as a stopper for a blood testing bottomed tube made of glass or, plastics such as polyethylene terephthalate, nylon, polypropylene, polyethylene, polystyrene, polycarbonate, hard vinyl chloride, acryl resin and the like. Particularly, by combination with a blood testing bottomed tube of the present invention, a higher effect is obtained.

A blood testing container comprising the blood testing bottomed tube according to the first or second aspect of the present invention and the stopper for a blood testing bottomed tube according to the third or fourth aspect of the present invention is also one of the present invention.

Thus, by use of a blood testing bottomed tube of the present invention and a stopper for a blood testing bottomed tube of the present invention in combination, a further excellent effect can be manifested in a blood test.

When the blood testing container of the present invention is a blood collecting tube, the pressure in the blood testing container can be reduced to give a vacuum blood collecting tube. Further, various chemicals are allowed to be accommodated in a blood testing container of the present invention depending on the object. The above-mentioned chemical is not particularly restricted, and there are mentioned, for example, a coagulation accelerator for collecting serum, a clot peeling agent for peeling of blood from a tube easy, an anticoagulant for preventing coagulation of blood, and the like are listed, and a serum separating agent, plasma separating and the like may also be accommodated.

BEST MODE FOR CARRYING OUT THE INVENTION

The present invention will be illustrated further in detail referring to the following examples, but the scope of the present invention is not limited to only these examples.

Example 1

Polyoxypropylene butyl ether (viscosity: 49 mPs/25° C.) was dissolved in ethanol so as to give a concentration of 5 wt % to prepare coating liquid.

20 mg of the resulted coating liquid was sprayed on a bottomed tube made of polyethylene terephthalate having an outer diameter of 16 mm having an internal diameter of parts engaged with a stopper of 14 mmφ and a length of 100 mm, then, vacuum-dried at 35° C., to manufacture a blood collecting tube.

Example 2

A blood collecting tube was manufactured in the same manner as that of Example 1 except that polyoxypropylene butyl ether (viscosity: 527 mPs/25° C.) was dissolved in ethanol so as to give a concentration of 3 wt % to prepare coating liquid.

Example 3

A blood collecting tube was manufactured in the same manner as that of Example 1 except that polyoxypropylene butyl ether (viscosity: 1400 mPs/25° C.) was dissolved in ethanol so as to give a concentration of 1 wt % to prepare coating liquid.

Example 4

A blood collecting tube was manufactured in the same manner as that of Example 1 except that polyoxypropylene glyceryl ether (viscosity: 652 mPs/25° C.) was dissolved in ethanol so as to give a concentration of 0.5 wt % to prepare coating liquid.

Example 5

A blood collecting tube was manufactured in the same manner as that of Example 1 except that polyoxypropylene glyceryl ether (viscosity: 652 mPs/25° C.) was dissolved in ethanol so as to give a concentration of 5 wt % to prepare coating liquid.

Example 6

A blood collecting tube was manufactured in the same manner as that of Example 1 except that polyoxypropylene butyl ether (viscosity: 527 mPs/25° C.) and polyoxypropylene glyceryl ether (viscosity: 652 mPs/25° C.) were dissolved in ethanol so as to give concentrations of 1 wt % and 0.5 wt % respectively, to prepare coating liquid.

Example 7

A blood collecting tube was manufactured in the same manner as that of Example 1 except that polyoxypropylene butyl ether (viscosity: 527 mPs/25° C.) and polyoxypropylene glyceryl ether (viscosity: 652 mPs/25° C.) were dissolved in ethanol so as to give concentrations of 0.5 wt % and 0.5 wt % respectively, to prepare coating liquid.

Example 8

A blood collecting tube was manufactured in the same manner as that of Example 1 except that polyoxypropylene butyl ether (viscosity: 527 mPs/25° C.) and polyoxypropylene glyceryl ether (viscosity: 652 mPs/25° C.) were dissolved in ethanol so as to give concentrations of 2 wt % and 1 wt % respectively, to prepare coating liquid.

Example 9

A blood collecting tube was manufactured in the same manner as that of Example 1 except that polyoxypropylene butyl ether (viscosity: 199 mPs/25° C.) and polyoxypropylene glyceryl ether (viscosity: 250 mPs/25° C.) were dissolved in ethanol so as to give concentrations of 1 wt % and 1 wt %, respectively to prepare coating liquid.

Example 10

A blood collecting tube was manufactured in the same manner as that of Example 1 except that polyoxyethylene polyoxypropylene butyl ether (viscosity: 285 mPs/25° C.) was dissolved in ethanol so as to give a concentration of 2 wt % to prepare coating liquid.

Example 11

A blood collecting tube was manufactured in the same manner as that of Example 1 except that polyoxyethylene polyoxypropylene glyceryl ether (viscosity: 374 mPs/25° C.) was dissolved in ethanol so as to give a concentration of 2 wt % to prepare coating liquid.

Example 12

A blood collecting tube was manufactured in the same manner as that of Example 1 except that a polyoxyethylene-polyoxypropylene condensate (ethylene oxide content: 10 wt %, average molecular weight: 1100) was dissolved in ethanol so as to give a concentration of 3 wt % to prepare coating liquid.

Example 13

A blood collecting tube was manufactured in the same manner as that of Example 1 except that a polyoxyethylene-polyoxypropylene condensate (ethylene oxide content: 50 wt %, average molecular weight: 4600) was dissolved in ethanol so as to give a concentration of 5 wt % to prepare coating liquid.

Example 14

A blood collecting tube was manufactured in the same manner as that of Example 1 except that polyethylene glycol (average molecular weight: 400) was dissolved in ethanol so as to give a concentration of 1 wt % to prepare coating liquid.

Example 15

A blood collecting tube was manufactured in the same manner as that of Example 1 except that polypropylene glycol (average molecular weight: 1500) was dissolved in ethanol so as to give a concentration of 1 wt % to prepare coating liquid.

Comparative Example 1

A blood collecting tube was manufactured in the same manner as that of Example 1 except that a polyether-modified silicone oil (kinetic viscosity: 1200 cSt/25° C.) was dissolved in ethanol so as to give a concentration of 3 wt % to prepare coating liquid.

Comparative Example 2

A blood collecting tube was manufactured in the same manner as that of Example 1 except that polydimethylsiloxane (hydrophobic silicone oil, kinetic viscosity: 5000 cSt/25° C.) was dissolved in ethanol so as to give a concentration of 3 wt % to prepare coating liquid.

Comparative Example 3

The bottomed tube used in Example 1 obtained without coating was used as a blood collecting tube.

The blood collecting tubes manufactured in Examples 1 to 15 and Comparative Examples 1 to 3 were allowed to accommodate 0.5 mg of silica as a coagulation accelerator, then, plugged under reduce pressure with a stopper 12 made of brominated butyl rubber having an outer diameter of engaged parts of 15 mmφ shown in FIG. 1, to manufacture vacuum blood collecting tubes having a blood collecting amount of 5 mL, and the resulted vacuum blood collecting tubes were subjected to the following evaluations.

The results are shown in Table 1.

(Clot Peeling Property)

Using the vacuum blood collecting tube, blood collecting in vacuo was conducted so that the blood collecting amount was 5 mL. After coagulation and centrifugal separation, the wall surface in the tube was visually checked, and utterly no remaining of clot was evaluated as ⊚, remaining of clot but in insignificant range was evaluated as ○, and apparent remaining of clot was evaluated as X.

(Test Value)

Using the vacuum blood collecting tube, blood collecting in vacuo was conducted so that the blood collecting amount was 5 mL. After coagulation and centrifugal separation, a test was conducted using the separated serum and its test value was compared with the test value of the control, and utterly no influence on the test value was evaluated as ⊚, certain influence on the test value but in insignificant range was evaluated as ○, and significant influence on the test value was evaluated as X.

(Disappearance of Foam in Blood)

A vacuum blood collecting tube was manufactured in the same manner as the above-mentioned manufacturing of a vacuum blood collecting tube except that an anti-coagulant was accommodated instead of a coagulation accelerator, and using the resulted vacuum blood collecting tube, blood collecting under vacuum was conducted so that the blood collecting amount was 5 mL, then, inversion mixing was conducted five times, and disappearance of foam in blood within 1 minute was evaluated as ⊚, disappearance within 2 minutes was evaluated as ○, and no disappearance even after 2 minutes was evaluated as X.

TABLE 1

|  | Clot peeling property | Test value | Disappearance of foam in blood |
|---|---|---|---|
| Example 1 | ⊚ | ⊚ | ○ |
| Example 2 | ⊚ | ⊚ | ○ |
| Example 3 | ⊚ | ⊚ | ○ |
| Example 4 | ⊚ | ○ | ⊚ |
| Example 5 | ⊚ | ○ | ⊚ |
| Example 6 | ⊚ | ⊚ | ⊚ |

TABLE 1-continued

|  | Clot peeling property | Test value | Disappearance of foam in blood |
|---|---|---|---|
| Example 7 | ◎ | ◎ | ◎ |
| Example 8 | ◎ | ◎ | ◎ |
| Example 9 | ◎ | ◎ | ◎ |
| Example 10 | ◎ | ○ | ◎ |
| Example 11 | ◎ | ○ | ◎ |
| Example 12 | ○ | ○ | ◎ |
| Example 13 | ○ | ○ | ◎ |
| Example 14 | ○ | ○ | ○ |
| Example 15 | ○ | ○ | ○ |
| Comparative Example 1 | ◎ | X | ◎ |
| Comparative Example 2 | ○ | X | X |
| Comparative Example 3 | X | X | X |

From Table 1, it was found that the blood collecting tubes manufactured in Examples 1 to 15 were excellent in no influence on clot peeling property and test value. Further, foam in blood did not occur, and even in the case of occurrence, it was de-foamed quickly.

The blood collecting tube coated with a modified silicone oil conventionally used manufactured in Comparative Example 1 was excellent in a clot peeling property, however, it exerted an influence on the test value. The blood collecting tube coated with polydimethylsiloxane (hydrophobic silicone oil) conventionally used manufactured in Comparative Example 2 had deficiencies in the test value and disappearance of foam in blood. Further, the blood collecting tube manufactured in Comparative Example 3 without coating was poor also in a clot peeling property in addition to an influence on the test value, and the blood collecting tubes in Comparative Examples 1 to 3 were not suitable as a blood testing bottomed tube.

Example 16

Polyoxypropylene butyl ether (viscosity: 49 mPs/25° C.) was dissolved in ethanol so as to give a concentration of 5 wt % to prepare coating liquid.

A member in the form of plug made of brominated butyl rubber was immersed into the resulted coating liquid, then, vacuum-dried at 35° C., to manufacture a stopper for blood collecting tube having an outer diameter of parts engaged with a tube body of 15 mmφ.

Example 17

A stopper for blood collecting tube was manufactured in the same manner as that of Example 16 except that polyoxypropylene butyl ether (viscosity: 527 mPs/25° C.) was dissolved in ethanol so as to give a concentration of 3 wt % to prepare coating liquid.

Example 18

A stopper for blood collecting tube was manufactured in the same manner as that of Example 16 except that polyoxypropylene butyl ether (viscosity: 1400 mPs/25° C.) was dissolved in ethanol so as to give a concentration of 1 wt % to prepare coating liquid.

Example 19

A stopper for blood collecting tube was manufactured in the same manner as that of Example 16 except that polyoxypropylene glyceryl ether (viscosity: 652 mPs/25° C.) was dissolved in ethanol so as to give a concentration of 0.5 wt % to prepare coating liquid.

Example 20

A stopper for blood collecting tube was manufactured in the same manner as that of Example 16 except that polyoxypropylene glyceryl ether (viscosity: 652 mPs/25° C.) was dissolved in ethanol so as to give a concentration of 5 wt % to prepare coating liquid.

Example 21

A stopper for blood collecting tube was manufactured in the same manner as that of Example 16 except that polyoxypropylene butyl ether (viscosity: 527 mPs/25° C.) and polyoxypropylene glyceryl ether (viscosity: 652 mPs/25° C.) were dissolved in ethanol so as to give concentrations of 1 wt % and 0.5 wt % respectively, to prepare coating liquid.

Example 22

A stopper for blood collecting tube was manufactured in the same manner as that of Example 16 except that polyoxypropylene butyl ether (viscosity: 527 mPs/25° C.) and polyoxypropylene glyceryl ether (viscosity: 652 mPs/25° C.) were dissolved in ethanol so as to give concentrations of 0.5 wt % and 0.5 wt % respectively, to prepare coating liquid.

Example 23

A stopper for blood collecting tube was manufactured in the same manner as that of Example 16 except that polyoxypropylene butyl ether (viscosity: 527 mPs/25° C.) and polyoxypropylene glyceryl ether (viscosity: 652 mPs/25° C.) were dissolved in ethanol so as to give concentrations of 2 wt % and 1 wt % respectively, to prepare coating liquid.

Example 24

A stopper for blood collecting tube was manufactured in the same manner as that of Example 16 except that polyoxypropylene butyl ether (viscosity: 199 mPs/25° C.) and polyoxypropylene glyceryl ether (viscosity: 250 mPs/25° C.) were dissolved in ethanol so as to give concentrations of 1 wt % and 1 wt % respectively, to prepare coating liquid.

Example 25

A stopper for blood collecting tube was manufactured in the same manner as that of Example 16 except that polyoxyethylene polyoxypropylene butyl ether (viscosity: 285 mPs/25° C.) was dissolved in ethanol so as to give a concentration of 2 wt % to prepare coating liquid.

Example 26

A stopper for blood collecting tube was manufactured in the same manner as that of Example 16 except that polyoxyethylene polyoxypropylene glyceryl ether (viscosity: 374 mPs/25° C.) was dissolved in ethanol so as to give a concentration of 2 wt % to prepare coating liquid.

Example 27

A stopper for blood collecting tube was manufactured in the same manner as that of Example 16 except that a polyoxyethylene-polyoxypropylene condensate (ethylene oxide content: 10 wt %, average molecular weight: 1100) was dissolved in ethanol so as to give a concentration of 3 wt % to prepare coating liquid.

Example 28

A stopper for blood collecting tube was manufactured in the same manner as that of Example 16 except that a polyoxyethylene-polyoxypropylene condensate (ethylene oxide content: 50 wt %, average molecular weight: 4600) was dissolved in ethanol so as to give a concentration of 5 wt % to prepare coating liquid.

Example 29

A stopper for blood collecting tube was manufactured in the same manner as that of Example 16 except that polyethylene glycol (average molecular weight: 400) was dissolved in ethanol so as to give a concentration of 1 wt % to prepare coating liquid.

Example 30

A stopper for blood collecting tube was manufactured in the same manner as that of Example 16 except that polypropylene glycol (average molecular weight: 1500) was dissolved in ethanol so as to give a concentration of 1 wt % to prepare coating liquid.

Comparative Example 4

A stopper for blood collecting tube was manufactured in the same manner as that of Example 16 except that a polyether-modified silicone oil (kinetic viscosity: 1200 cSt/25° C.) was dissolved in ethanol so as to give a concentration of 3 wt % to prepare coating liquid.

Comparative Example 5

A stopper for blood collecting tube was manufactured in the same manner as that of Example 16 except that polydimethylsiloxane (hydrophobic silicone oil, kinetic viscosity: 5000 cSt/25° C.) was dissolved in ethanol so as to give a concentration of 3 wt % to prepare coating liquid.

Comparative Example 6

The member in the form of plug used in Example 16 obtained without coating was used as a stopper for blood collecting tube.

The stoppers for blood collecting tube manufactured in Examples 16 to 30 and Comparative Examples 4 to 6 were subjected to the following evaluations using a bottomed tube 11 made of polyethylene terephthalate having an internal diameter of 14 mm, an outer diameter of 16 mm and a length of 100 mm shown in FIG. 1 as a blood collecting tube.

The results are shown in Table 2.

(Lubricity)

Whether the blood collecting tube can be plugged with the stopper was checked, and very easy plugging was evaluated as ◎, easy plugging was evaluated as ○, and not easy plugging was evaluated as X.

(Clot Peeling Property)

Using the vacuum blood collecting tube manufactured by plugging a blood collection tube treated with a coagulation accelerator and a clot peeling agent with a stopper under reduced pressure, blood collecting in vacuo was conducted so that the blood collecting amount was 5 mL. After coagulation and centrifugal separation, the stopper was visually checked, and utterly no remaining of clot was evaluated as ◎, remaining of clot but in insignificant range was evaluated as ○, and apparent remaining of clot was evaluated as X.

(Test Value)

Using the vacuum blood collecting tube manufactured by plugging a blood collection tube treated with a coagulation accelerator and a clot peeling agent with a stopper under reduced pressure, blood collecting in vacuo was conducted so that the blood collecting amount was 5 mL. After coagulation and centrifugal separation, a test was conducted using the separated serum and its test value was compared with the test value of the control, and utterly no influence on the test value was evaluated as ◎, certain influence on the test value but in insignificant range was evaluated as ○, and significant influence on the test value was evaluated as X.

(Label Adhesiveness)

20 stoppers and 5 blood collecting tubes were sufficiently shaken in a plastic bag, then, the blood collecting tubes were taken out and a specimen label was pasted on the outer peripheral curve. After left for 24 hours, the condition of the label was visually checked, and utterly no peeling was evaluated by ◎, partially peeling was evaluated as ○, and almost peeling was evaluated as X.

(Disappearance of Foam in Blood)

A blood collecting tube containing an anti-coagulant was plugged with a stopper, and using the resulted vacuum blood collecting tube, blood collecting under vacuum was conducted so that the blood collecting amount was 5 mL, then, inversion mixing was conducted five times, and disappearance of foam in blood within 1 minute was evaluated as ◎, disappearance within 2 minutes was evaluated as ○, and no disappearance even after 2 minutes was evaluated as X.

TABLE 2

| | Lubricity | Clot peeling property | Test value | Label adhesiveness | Disappearance of foam in blood |
|---|---|---|---|---|---|
| Example 16 | ◎ | ◎ | ◎ | ◎ | ○ |
| Example 17 | ◎ | ◎ | ◎ | ◎ | ○ |
| Example 18 | ◎ | ◎ | ◎ | ◎ | ○ |
| Example 19 | ◎ | ◎ | ○ | ◎ | ◎ |
| Example 20 | ◎ | ◎ | ○ | ◎ | ◎ |
| Example 21 | ◎ | ◎ | ◎ | ◎ | ◎ |
| Example 22 | ◎ | ◎ | ◎ | ◎ | ◎ |
| Example 23 | ◎ | ◎ | ◎ | ◎ | ◎ |
| Example 24 | ◎ | ◎ | ◎ | ◎ | ◎ |
| Example 25 | ◎ | ◎ | ○ | ○ | ◎ |
| Example 26 | ◎ | ◎ | ○ | ○ | ◎ |

TABLE 2-continued

|  | Lubricity | Clot peeling property | Test value | Label adhesiveness | Disappearance of foam in blood |
|---|---|---|---|---|---|
| Example 27 | ◎ | ○ | ○ | ○ | ◎ |
| Example 28 | ◎ | ○ | ○ | ○ | ◎ |
| Example 29 | ◎ | ○ | ○ | ○ | ○ |
| Example 30 | ◎ | ○ | ○ | ○ | ○ |
| Comparative Example 4 | ◎ | ◎ | X | X | ◎ |
| Comparative Example 5 | ◎ | ○ | X | X | X |
| Comparative Example 6 | X | X | X | ◎ | X |

From Table 2, it was found that the stoppers manufactured in Examples 16 to 30 were excellent in no influence on lubricity, clot peeling property and test value, and in label adhesiveness. Further, foam in blood did not occur, and even in the case of occurrence, it was de-foamed quickly.

The stopper coated with a modified silicone oil conventionally used manufactured in Comparative Example 4 was excellent in lubricity and a clot peeling property, however, it exerted an influence on the test value and poor in label adhesiveness. The stopper coated with polydimethylsiloxane (hydrophobic silicone oil) conventionally used manufactured in Comparative Example 5 had deficiencies in the test value, label peeling and disappearance of foam in blood. Further, the stopper manufactured in Comparative Example 6 without coating was poor also in lubricity, clot peeling property and disappearance of foam in blood, in addition to an influence on the test value, and the stoppers in Comparative Examples 4 to 6 were not suitable as a stopper for a blood testing bottomed tube.

INDUSTRIAL APPLICABILITY

According the present invention, a blood testing bottomed tube which causes no adhesion of blood clot and the like and no foam in blood in a blood test, and even in the case of generation of foam in blood, de-foams this quickly, and does not exert an influence on the test value, a stopper for a blood testing bottomed tube which can plug a blood testing bottomed tube easily, causes no adhesion of blood clot and the like and no foam in blood in a blood test, and even in the case of generation of foam in blood, de-foams this quickly, and does not exert an influence on the test value, further, does not cause label peeling and stickiness on a blood testing bottomed tube, and a blood testing container comprising the above-mentioned blood testing bottomed tube and the above-mentioned stopper for a blood testing bottomed tube, can be provided.

The invention claimed is:

1. A method of de-foaming blood for a blood test and causing no adhesion of blood clots which comprises:
a step of preparing a blood testing container by plugging a blood testing bottomed tube comprising a tubular member having an open one end and closed another end, and a coating layer formed on at least a part to be contacted with blood on said tubular member, said coating layer being made of the compound selected from the group consisting of a polyoxypropylene butyl ether, a polyoxypropylene glyceryl ether, a polyoxyethylene polyoxypropylene butyl ether, and a polyoxyethylene polyoxypropylene glyceryl ether with a stopper for a blood testing bottomed tube and reducing pressure;
a step of collecting blood into the blood testing container; and
a step of causing no foaming in blood, de-foaming blood quickly and causing no adhesion of blood clots to the walls of said tubular member, said step being performed by contacting blood with said coating layer, and wherein said causing no foaming in blood, de-foaming blood quickly and causing no adhesion of blood clots to the walls of said tubular member is caused by said compound.

2. A method of de-foaming blood for a blood test and causing no adhesion of blood clots-which comprises:
a step of preparing a blood testing container by plugging a blood testing bottomed tube comprising a tubular member having an open one end and closed another end with a stopper for a blood testing bottomed tube comprising a member in the form of plug, and a coating layer made of the compound selected from the group consisting of a polyoxypropylene butyl ether, a polyoxypropylene glyceryl ether, a polyoxyethylene polyoxypropylene butyl ether, and a polyoxyethylene polyoxypropylene glyceryl ether formed on the surface of said member in the form of plug and reducing pressure;
a step of collecting blood into the blood testing container; and
a step of causing no foaming in blood, de-foaming blood quickly and causing no adhesion of blood clots to the walls of said tubular member, said step being performed by contacting blood with said coating layer, and wherein said causing no foaming in blood, de-foaming blood quickly and causing no adhesion of blood clots to the walls of said tubular member is caused by said compound.

3. A method of de-foaming blood for a blood test and causing no adhesion of blood clots which comprises:
a step of preparing a blood testing container by plugging a blood testing bottomed tube comprising a tubular member having an open one end and closed another end, and a coating layer formed on at least a part to be contacted with blood on said tubular member, said coating layer being made of the compound selected from the group consisting of a polyoxypropylene butyl ether, a polyoxypropylene glyceryl ether, a polyoxyethylene polyoxypropylene butyl ether, and a polyoxyethylene polyoxypropylene glyceryl ether with a stopper for a blood testing bottomed tube comprising a member in the form of plug, and a coating layer made of the compound selected from the group consisting of a polyoxypropylene butyl ether, a polyoxypropylene glyceryl ether, a polyoxyethylene polyoxypropylene butyl ether, and a polyoxyethylene polyoxypropylene glyceryl ether-formed on the surface of said member in the form of plug and reducing pressure;

a step of collecting blood into the blood testing container; and a step of causing no foaming in blood, de-foaming blood quickly and causing no adhesion of blood clots to the walls of said tubular member, said step being performed by contacting blood with said coating layer, and wherein said causing no foaming in blood, de-foaming blood quickly and causing no adhesion of blood clots to the walls of said tubular member is caused by said compound.

* * * * *